United States Patent
Mihan

(10) Patent No.: US 7,838,607 B2
(45) Date of Patent: Nov. 23, 2010

(54) ANTISTATIC FOR OLEFIN POLYMERIZATION AND PROCESS FOR PREPARING IT

(75) Inventor: Shahram Mihan, Bad Soden (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 12/226,384

(22) PCT Filed: May 4, 2007

(86) PCT No.: PCT/EP2007/003944

§ 371 (c)(1),
(2), (4) Date: Oct. 17, 2008

(87) PCT Pub. No.: WO2007/131646

PCT Pub. Date: Nov. 22, 2007

(65) Prior Publication Data

US 2009/0105428 A1     Apr. 23, 2009

Related U.S. Application Data

(60) Provisional application No. 60/811,014, filed on Jun. 5, 2006.

(30) Foreign Application Priority Data

May 11, 2006    (DE) .................... 10 2006 022 255

(51) Int. Cl.
*C08F 4/44* (2006.01)
*C08F 2/00* (2006.01)

(52) U.S. Cl. .................. 526/142; 526/74; 526/160; 526/217; 526/222; 526/225

(58) Field of Classification Search .......... 526/85, 526/86, 90, 177, 234, 74, 142, 160
See application file for complete search history.

(56) References Cited

U.S. PATENT DOCUMENTS

| | | | |
|---|---|---|---|
| 3,242,150 A | 3/1966 | Scoggin | 260/88.2 |
| 3,248,179 A | 4/1966 | Norwood | 23/285 |
| 3,917,466 A | 11/1975 | Henry, Jr. | 44/62 |
| 4,182,810 A | 1/1980 | Willcox | 526/64 |
| 4,675,368 A | 6/1987 | Bienfait et al. | 526/75 |
| 5,026,795 A | 6/1991 | Hogan | 526/74 |
| 5,194,526 A | 3/1993 | Hussein et al. | 526/74 |
| 5,283,278 A | 2/1994 | Daire et al. | 524/399 |
| 5,319,009 A | 6/1994 | Brokken-Zijp et al. | 524/236 |
| 5,391,657 A | 2/1995 | Song et al. | 526/74 |
| 5,414,064 A | 5/1995 | Lux et al. | 526/215 |
| 5,455,216 A | 10/1995 | Mueller et al. | 502/256 |
| 5,698,642 A | 12/1997 | Govoni et al. | 526/65 |
| 6,562,924 B2 | 5/2003 | Benazouzz et al. | 526/201 |
| 6,689,845 B1 | 2/2004 | Govoni et al. | 526/65 |
| 6,803,430 B2 | 10/2004 | Agapiou et al. | 526/142 |
| 6,894,127 B2 * | 5/2005 | Behue et al. | 526/90 |
| 6,924,248 B2 | 8/2005 | Mihan et al. | 502/132 |
| 6,936,666 B2 | 8/2005 | Mihan et al. | 526/68 |
| 2005/0203265 A1 * | 9/2005 | Sukhadia et al. | 526/348.1 |

FOREIGN PATENT DOCUMENTS

| | | |
|---|---|---|
| DE | 3108843 | 3/1981 |
| DE | 3543360 | 12/1985 |
| FR | 2478654 | 3/1981 |
| WO | WO 0144323 A1 * | 6/2001 |

* cited by examiner

*Primary Examiner*—David Wu
*Assistant Examiner*—Elizabeth Eng
(74) *Attorney, Agent, or Firm*—Shao-Hua Guo

(57) ABSTRACT

Process for preparing an antistatic for olefin polymerization by contacting an antistatically acting compound comprising at least one hydrogen atom bound to a nonmetallic heteroatom with at least one metal alkyl in an amount which is sufficient to react completely with the at least one hydrogen atom bound to a heteroatom, wherein the antistatically acting compound and the metal alkyl are each present in a concentration of at least 0.01% by weight during contacting.

19 Claims, No Drawings

ANTISTATIC FOR OLEFIN POLYMERIZATION AND PROCESS FOR PREPARING IT

CROSS-REFERENCE TO RELATED APPLICATIONS:

This application is the U.S. national stage under 35 U.S.C. §371 of International Application PCT/EP2007/003944, filed May 4, 2007, claiming priority to German Patent Application No. 10 2006 022 255.5, filed May 11, 2006, and provisional U.S. Appl. No. 60/811,014, filed June 5, 2006; the disclosures of International Application PCT/EP2007/003944, German Patent Application No. 10 2006 022 255.5, and provisional U.S. Appl. No. 60/811,014, each as filed, are incorporated herein by reference.

The invention relates to a process for preparing an antistatic for olefin polymerization, a corresponding antistatic and a process for olefin polymerization.

In the continuous polymerization of olefins, antistatics are used to avoid electrostatic charging. The antistatically acting compounds comprised in these generally comprise organic compounds having polar functional groups such as acid or ester groups, amine or amide groups or hydroxyl or ether groups. Examples of constituents of typical antistatics are polysulfone copolymers, polymeric polyamines, oil-soluble sulfonic acids, polysiloxanes, alkoxyamines, polyglycol ethers, etc.

Furthermore, metal alkyls are usually used as scavengers in olefin polymerization in order to protect the catalyst from being destroyed by the ever-present traces of polar compounds in the reactor. The scavengers react with the impurities before they can have an effect on the catalyst. A satisfactory activity is ensured in this way.

A disadvantage of all previous antistatics is that they not only have the desired antistatic action but also have a pronounced negative effect on the reactivity of virtually all olefin polymerization catalysts.

To reduce these negative effects, it has been proposed, for example, in EP-A-1 255 783, to introduce a carboxylic acid and a metal alkyl into the reactor in parallel with metallocene catalysts in order to produce a metal carboxylate salt, which is known to have an antistatic action, in situ in the reactor.

Even if the poisoning action of the antistatic can be reduced in this way, pronounced deactivation of the sensitive transition metal catalyst component is still always observed. This is more pronounced, the smaller the amount of metal alkyl or metal aluminoxane used.

It was therefore an object of the present invention to overcome the abovementioned disadvantages of the prior art and to provide an antistatic for olefin polymerization which has a good or even improved antistatic action with a reduced deactivating action on the catalyst.

It has now surprisingly been found that conventional antistatically acting compounds which have been reacted with metal alkyls before use display a significantly reduced deactivating action with improved conductivity and thus antistatic action.

Accordingly, this object is achieved by a process for preparing an antistatic for olefin polymerization by contacting a) at least one antistatically acting compound comprising at least one hydrogen atom bound to a nonmetallic heteroatom with b) at least one metal alkyl in an amount which is sufficient to react completely with the at least one hydrogen atom bound to a heteroatom, wherein the at least one antistatically acting compound and the at least one metal alkyl are each present in a concentration of at least 0.01% by weight during contacting. When mixtures of antistatic compounds and/or metal alkyls are used, the concentration is based on the sum of the antistatically acting compounds comprising at least one hydrogen atom bound to a nonmetallic heteroatom or the sum of the metal alkyls.

Compared to the customary in-situ reaction of the metal alkyls with an antistatic in the polymerization reactor itself, the concentrations of the antistatic and of the metal alkyl are significantly higher in the process of the invention. This increase in concentration leads to an increase in the rate constant by a number of orders of magnitude, so that essentially complete reaction of the hydrogen atoms bound to a nonmetallic heteroatom in the antistatic, hereinafter also referred to as active hydrogen, is presumably made kinetically possible. Secondly, the lack of competition for between the metal alkyl and the catalyst by the active hydrogen in the antistatic, which is likewise suppressed by the prior contacting of the conventional antistatically acting compound with the metal alkyl, could be a reason for the improved properties of the antistatic prepared in this way, without wishing to be tied to this explanation.

For the purposes of the present invention, an antistatically acting compound is a chemical compound which is able to reduce negative or positive electrostatic charges in the reactor. It can be a single chemical compound or preferably also a mixture of a plurality of antistatically acting compounds. According to the invention, the at least one antistatically acting compound has at least one hydrogen atom bound to a nonmetallic heteroatom, hereinafter referred to as active hydrogen. Heteroatoms can in principle be all nonmetallic heteroatoms which are at least divalent and can therefore not only form a bond to a carbon but can additionally bond to at least one hydrogen atom. Preferred nonmetallic heteroatoms are O, N, S and P.

The at least one antistatically acting compound preferably has an electrical conductivity of at least 0.05 µS/cm, more preferably at least 0.10 µS/cm, more preferably at least 0.20 µS/cm, more preferably 0.50 µS/cm, particularly preferably 1.0 µS/cm. In the case of mixtures, at least one of the components should have a corresponding conductivity.

Preferred antistatically acting compounds are those having a molar mass of at least 100 g/mol, more preferably at least 150 g/mol, particularly preferably at least 200 g/mol, with mixtures comprising at least one such antistatically acting compound also being preferred.

Further preference is given to organic antistatically acting compounds, with those having at least 5, in particular at least 10, carbon atoms being particularly advantageous.

The antistatically acting compound preferably has hydrogen-comprising functional groups selected from among —OH, —COOH, —NH$_2$, —NHR$^1$, —SH, —PH$_2$, —PHR$^1$ and —SO$_3$H, where R$^1$ is an alkyl, aryl, alkylaryl or arylalkyl radical in which one or more carbon atoms may also be replaced by heteroatoms.

In addition, further functional groups which do not bear any hydrogen, e.g. —OR$^1$, —COOR$^1$, —SO$_3$R$^1$, —SiO$_2$R$^1$, —NR$^1$R$^2$, —CHO, —CO—R$^1$, where R$^1$ and R$^2$ are each, independently of one another, an alkyl, aryl, alkylaryl or arylalkyl radical in which one or more carbon atoms may also be replaced by heteroatoms and the radicals R$^1$ and R$^2$ may together form a ring, can preferably also be present.

Particularly preferred antistatically acting compounds are those comprising higher polyhydric alcohols and their ethers, for example sorbitol, polyalcohols, polyalcohol ethers, polyvinyl alcohols, polyethylene glycols and their ethers with fatty alcohols, carboxylic acids, anion-active substances such as $C_{12}$-$C_{22}$-fatty acid soaps of alkali or alkaline earth metals, salts of alkylsulfates of higher primary or secondary alcohols having the general formula ROSO$_3$M (M=alkali metal, alkaline earth metal, R=alkyl, aryl, arylalkyl or alkylaryl) or (RR') CHOSO$_3$M, salts of mixed esters of polyfunctional alcohols with higher fatty acids and sulfuric acid, $C_{12}$-$C_{22}$-sulfonic acids or their salts of the general formula R$^1$SO$_3$M, alkylarylsulfonic acids or their salts, e.g. dodecylbenzenesulfonic acid, phosphoric acid derivatives such as di(alkoxypolyethoxyethyl)phosphates of the general formula [RO(CH$_2$CH$_2$O)$_n$]$_2$POOM or phytic acid derivatives as disclosed, for example, in EP-A 453116, cation-active deactivators such as quaternary ammonium salts of the general formula R$^1$R$^2$R$^3$R$^4$NX, where X is a halogen atom and R$^1$ to R$^4$ are, independently of one another, an alkyl radical, preferably one having at least 8 carbon atoms. Also suitable are, for example, metal complexes such as the cyanophthalocyanines disclosed in WO 93/24562.

Particularly useful antistatically acting compounds are nonvolatile nitrogen-comprising compounds such as amines or amides or their salts, in particular oligomeric or polymeric amines and amides. Examples which may be mentioned are polyethoxyalkylamines or polyethoxyalkylamides of the general formula R$^1$N[(R$^2$O)$_m$R][(R$^3$O)$_n$H] or R$^1$CON [(R$_2$O)$_m$R][(R$^3$O)$_n$H], where R$^1$ to R$^3$ are alkyl radicals, in the case of R$^1$ preferably alkyl radicals having at least 8 carbon atoms, preferably at least 12 carbon atoms, and n, m are equal to or greater than 1, as described in DE-A 31 088 43. These are also constituents of commercial antistatics (e.g. Atmer® 163; from Uniqema). It is also possible to use salt mixtures comprising calcium salts of Medialanic acid and chromium salts of N-stearylanthranilic acid, as described in DE-A 3543360, or mixtures of a metal salt of Medialanic acid, a metal salt of anthranilic acid and a polyamine as described in EP-A 636 636.

Further particularly useful antistatically acting compounds are polyamines or polyamine copolymers or mixtures of such compounds with further compounds, in particular polymeric compounds. Apart from simple polyamines such as polyvinylamine, suitable nonvolatile polyamines are advantageously obtained from the reaction of aliphatic primary monoamines such as n-octylamine or n-dodecylamine or N-alkyl-substituted aliphatic diamines such as N-n-hexadecyl-1,3-propanediamine and epichlorohydrin. These polyaminopolyols have not only amino groups but also hydroxyl groups. An overview of such polyamine copolymers is given in U.S. Pat. No. 3,917,466. Polysulfone copolymers are particularly suitable polymers for use together with polyamines or polyamine copolymers. The polysulfone copolymers are preferably largely unbranched and are made up of olefins and SO$_2$ units in a molar ratio of 1:1. An overview of suitable polysulfone copolymers is also given in U.S. Pat. No. 3,917,466. 1-Decene polysulfone may be mentioned by way of example. Mixtures comprising polysulfone copolymers, a polyamine and a long-chain sulfonic acid are described in U.S. Pat. No. 5,026,795 and U.S. Pat. No. 4,182,810.

In a particularly preferred embodiment, the at least one antistatically acting compound comprises a polysulfone copolymer, a polymeric polyamine and an oil-soluble sulfonic acid. Mixtures of this type are described, for example, in WO 00/68274 or WO 02/040554. Reaction of these mixtures results, in particular, in the oil-soluble sulfonic acid comprising active hydrogen being converted into a compound which does not comprise any active hydrogen. Preferred sulfonic acids are monosubstituted or disubstituted phenylsulfonic or naphthylsulfonic acids.

Further antistatically acting compounds may be found in FR 2478654, U.S. Pat. No. 5,026,795, EP-A 453116, U.S. Pat. No. 4,675,368, EP-A 584574 or U.S. Pat. No. 5,391,657.

In one embodiment of the present invention, the antistatic comprises an oil-soluble metal alkylsulfonate which can be prepared by reacting a metal alkyl with such an oil-soluble sulfonic acid. The antistatic particularly preferably further comprises a polysulfone copolymer and a polymeric polyamine.

For the purposes of the present invention, metal alkyls are compounds of metals or semimetals with linear or cyclic alkyls, aryls, alkylaryls and/or arylalkyls which are able to react with the active hydrogen of the antistatics. It is also possible to use mixtures of metal alkyls here. Suitable metal alkyls are those of the general formula (I),

$$M^G(R^{1G})_{r^G}(R^{2G})_{s^G}(R^{3G})_{t^G} \qquad (I)$$

where $M^G$ is Li, Na, K, Be, Mg, Ca, Sr, Ba, boron, aluminum, gallium, indium, thallium, zinc, in particular Li, Na, K, Mg, boron, aluminum or Zn, $R^{1G}$ is hydrogen, $C_1$-$C_{10}$-alkyl, $C_6$-$C_{15}$-aryl, alkylaryl or arylalkyl each having from 1 to 10 carbon atoms in the alkyl radical and from 6 to 20 carbon atoms in the aryl radical, $R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl radical and from 6 to 20 carbon atoms in the aryl radical, or alkoxy with $C_1$-$C_{10}$-alkyl or $C_6$-$C_{15}$-aryl, $r^G$ is an integer from 1 to 3 and $s^G$ and $t^G$ are integers in the range from 0 to 2, with the sum $r^G$+$s^G$+$t^G$ corresponding to the valence of $M^G$, with the metal alkyls usually not being identical to the activators for the catalysts. It is also possible to use mixtures of various metal alkyls of the formula (I).

Among the metal alkyls of the general formula (I), preference is given to those in which $M^G$ is lithium, magnesium, boron or aluminum and $R^{1G}$ is $C_1$-$C_{20}$-alkyl.

Particularly preferred metal alkyls of the formula (I) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

Most useful metal alkyls are triethylaluminum, trimethylaluminum, trihexylaluminum and butyllithium.

The antistatically acting compound and the metal alkyl are brought into contact in a concentration of in each case at least 0.01% by weight, preferably at least 0.05% by weight, particularly preferably at least 0.1% by weight, in order to ensure sufficient reaction. A relatively high concentration is particularly important in the case of short contact times. The antistatically acting compound and the metal alkyl can be used in diluted or undiluted form, with the use of a solution being preferred. Use in an inert hydrocarbon or the monomer or one of the monomers is particularly preferred.

The antistatically acting compound and the metal alkyl can, for example, be present in pure form, in solution or in suspension during contacting. One of the two components can also be present in supported form.

The metal alkyl is used in an amount which is sufficient to bind the hydrogen bound to heteroatoms, hereinafter also referred to as active hydrogen. Particularly good results are achieved when the metal alkyl is used in an at least stoichiometric amount relative to the active hydrogen comprised in the antistatic compound. Particular preference is given to an excess of from 1.1 to 1.5 times the stoichiometric amount.

The antistatic prepared in this way can be introduced into the reactor with the aid of all customary methods. The antistatic can be introduced into the reactor separately from other materials. However, it is preferably introduced as a solution in an inert solvent such as alkanes.

It can be introduced directly into the reactor or into a line leading to the reactor.

The preparation of the antistatic by contacting the antistatically acting compound with a metal alkyl can be carried out in a separate apparatus prior to the polymerization, but preference is given to preparing the antistatic in the reactor immediately before use. Particular preference is given to carrying out contacting in a line leading to the reactor or a vessel connected to such a line.

Contacting is carried out before the antistatic compound can come into contact with the catalyst and the contact time should be sufficient to ensure complete reaction of the active hydrogen. Contacting of the antistatically acting compound with the metal alkyl is preferably carried out for at least 5 s before introduction into the reactor. Preference is given to a contact time of from 10 s to 10 h, more preferably from 15 s to 1 h, particularly preferably from 20 s to 30 min, before introduction into the reactor.

The present invention further provides a process for the polymerization of unsaturated monomers, in particular 1-olefins, at temperatures of from 20 to 200° C. and pressures of from 0.1 to 20 MPa in the presence of a polymerization catalyst using the antistatic mixture of the invention.

The process is suitable, in particular, for the polymerization of olefins and especially for the polymerization of 1-olefins (α-olefins), i.e. hydrocarbons having terminal double bonds, without being restricted thereto. Suitable monomers can be functionalized olefinically unsaturated compounds such as ester or amide derivatives of acrylic or methacrylic acid, for example acrylates, methacrylates, or acrylonitrile. Preference is given to nonpolar olefinic compounds, including aryl-substituted 1-olefins. Particularly preferred 1-olefins are linear or branched $C_2$-$C_{12}$-1-alkenes, in particular linear $C_2$-$C_{10}$-1-alkenes such as ethylene, propylene, 1-butene, 1-pentene, 1-hexene, 1-heptene, 1-octene, 1-decene or branched $C_2$-$C_{10}$-1-alkenes such as 4-methyl-1-pentene, conjugated and nonconjugated dienes such as 1,3-butadiene, 1,4-hexadiene or 1,7-octadiene or vinylaromatic compounds such as styrene or substituted styrene. It is also possible to polymerize mixtures of various α-olefins. Suitable olefins also include ones in which the double bond is part of a cyclic structure which can have one or more ring systems. Examples are cyclopentene, norbornene, tetracyclododecene or methylnorbornene or dienes such as 5-ethylidene-2-norbornene, norbornadiene or ethylnorbornadiene. It is also possible to polymerize mixtures of two or more olefins.

The process can be used in particular for the homopolymerization or copolymerization of ethylene or propylene. As comonomers in ethylene polymerization, preference is given to using up to 40% by weight of $C_3$-$C_8$-1-alkenes, in particular 1-butene, 1-pentene, 1-hexene and/or 1-octene. Preferred comonomers in propylene polymerization are up to 40% by weight of ethylene and/or butene. Particular preference is given to a process in which ethylene is copolymerized with up to 20% by weight of 1-hexene and/or 1-butene.

The polymerization of olefins can be carried out using all customary olefin polymerization catalysts. Preference is given to using single-site catalysts. For the purposes of the present invention, single-site catalysts are catalysts based on chemically uniform transition metal coordination compounds. Particularly suitable single-site catalysts are those comprising bulky sigma- or pi-bonded organic ligands, e.g. catalysts based on bis-cp or mono-cp complexes, hereinafter also referred to collectively as metallocene catalysts, or catalysts based on later transition metal complexes, in particular iron-bisimine complexes.

Furthermore, it is also possible to use Phillips catalysts based on chromium oxide or Ti-based Ziegler catalysts. The preparation and use of the known catalysts in olefin polymerization are generally known.

Preference is given to the process in combination with hybrid catalysts. For the purposes of the present invention, hybrid catalysts are catalyst systems which have at least two different types of active sites derived from at least two chemically different starting materials. The different active sites can be active sites which are comprised in various single-site catalysts. However, it is also possible to use active sites which are derived from Ziegler-Natta catalysts or catalysts based on chromium, e.g. Phillips catalysts.

Particularly preferred hybrid catalysts are those comprising late transition metal complexes, in particular iron-bisimine complexes, and at least one further mono-cp or bis-cp metallocene or a Ziegler catalyst.

The process can be carried out using all industrially known low-pressure polymerization methods at temperatures in the range from 0 to 200° C., preferably from 25 to 150° C. and particularly preferably from 40 to 130° C., and under pressures of from 0.05 to 10 MPa and particularly preferably from 0.3 to 4 MPa. The polymerization can be carried out batchwise or preferably continuously in one or more stages. Solution processes, suspension processes, stirred gas-phase processes and gas-phase fluidized-bed processes are all possible. Processes of this type are generally known to those skilled in the art. Among the polymerization processes mentioned, gas-phase polymerization, in particular in gas-phase fluidized-bed reactors, solution polymerization and suspension polymerization, in particular in loop reactors and stirred tank reactors, are preferred.

In the case of suspension polymerizations, polymerization is usually carried out in a suspension medium, preferably in an inert hydrocarbon such as isobutane or mixtures of hydrocarbons or else in the monomers themselves. Suspension polymerization temperatures are usually in the range from −20 to 115° C., and the pressure is in the range from 0.1 to 10 MPa. The solids content of the suspension is generally in the range from 10 to 80%. The polymerization can be carried out both batchwise, e.g. in stirring autoclaves, and continuously, e.g. in tube reactors, preferably in loop reactors. In particular, it can be carried out by the Phillips PF process as described in U.S. Pat. Nos. 3,242,150 and 3,248,179.

Suitable suspension media are all media which are generally known for use in suspension reactors. The suspension medium should be inert and be liquid or supercritical under the reaction conditions and should have a boiling point which is significantly different from those of the monomers and comonomers used in order to make it possible for these starting materials to be recovered from the product mixture by distillation. Customary suspension media are saturated hydrocarbons having from 4 to 12 carbon atoms, for example isobutane, butane, propane, isopentane, pentane and hexane, or a mixture of these, which is also known as diesel oil.

In a further, preferred suspension polymerization process, the polymerization takes place in a cascade of 2 or preferably 3 or 4 stirred vessels in the presence of a Ziegler catalyst. The molar mass of the polymer fraction prepared in each of the reactors is preferably set by addition of hydrogen to the reaction mixture. The polymerization process is preferably carried out with the highest hydrogen concentration and the lowest comonomer concentration, based on the amount of monomer, being set in the first reactor. In the subsequent further reactors, the hydrogen concentration is gradually reduced and the comonomer concentration is altered, in each case once again based on the amount of monomer. Ethylene or propylene is preferably used as monomer and a 1-olefin having from 4 to 10 carbon atoms is preferably used as comonomer.

Because the Ziegler catalyst generally suffers a reduction in its polymerization activity with rising hydrogen concentration and because a process-related dilution of the suspension with increasing total conversion occurs, the reacting polymer particles in the first reactor have the longest mean residence time. For this reason, the highest conversion of the added monomer to homopolymer or of the added monomer and comonomer to copolymer is achieved in the first reactor, compared to the downstream reactors.

In loop reactors, the polymerization mixture is pumped continuously through a cyclic reactor tube. As a result of the pumped circulation, continual mixing of the reaction mixture is achieved and the catalyst introduced and the monomers fed in are distributed in the reaction mixture. Furthermore, the pumped circulation prevents sedimentation of the suspended polymer. The removal of the heat of reaction via the reactor wall is also promoted by the pumped circulation. In general, these reactors consist essentially of a cyclic reactor tube having one or more ascending legs and one or more descending legs which are enclosed by cooling jackets for removal of the heat of reaction and also horizontal tube sections which connect the vertical legs. The impeller pump, the catalyst feed facilities and the monomer feed facilities and also the discharge facility, thus in general the settling legs, are usually installed in the lower tube section. However, the reactor can also have more than two vertical tube sections, so that a meandering arrangement is obtained.

The polymer is generally discharged continuously from the loop reactor via settling legs. The settling legs are vertical attachments which branch off from the lower reactor tube section and in which the polymer particles can sediment. After sedimentation of the polymer has occurred to a particular degree, a valve at the lower end of the settling legs is briefly opened and the sedimented polymer is discharged discontinuously.

In a preferred embodiment, the suspension polymerization is carried out in a loop reactor at an ethylene concentration of at least 10 mol %, preferably 15 mol %, particularly preferably 17 mol %, based on the suspension medium. For the purpose of these figures, the suspension medium is not the input suspension medium such as isobutane alone but rather the mixture of this input suspension medium with the monomers dissolved therein. The ethylene concentration can easily be determined by gas-chromatographic analysis of the suspension medium.

A preferred polymerization process is that carried out in a horizontally or vertically stirred or fluidized gas phase.

Particular preference is given to gas-phase polymerization in a fluidized-bed reactor, in which the circulated reactor gas is fed in at the lower end of a reactor and is taken off again at its upper end. When such a process is employed for the polymerization of 1-olefins, the circulated reactor gas is usually a mixture of the 1-olefin to be polymerized, if desired a molecular weight regulator such as hydrogen and inert gases such as nitrogen and/or lower alkanes such as ethane, propane, butane, pentane or hexane. The use of propane, if appropriate in combination with further lower alkanes, is preferred. The velocity of the reactor gas has to be sufficiently high firstly to fluidize the mixed bed of finely divided polymer present in the tube and serving as polymerization zone and secondly to remove the heat of polymerization effectively (noncondensed mode). The polymerization can also be carried out in the condensed or supercondensed mode, in which part of the circulating gas is cooled to below the dew point and returned to the reactor together as a two-phase mixture or separately as a liquid and a gas phase in order to make additional use of the enthalpy of vaporization for cooling the reaction gas.

In gas-phase fluidized-bed reactors, it is advisable to work at pressures of from 0.1 to 10 MPa, preferably 0.5 to 8 MPa and in particular from 1.0 to 3 MPa. In addition, the cooling capacity depends on the temperature at which the (co)polymerization in the fluidized bed is carried out. The process is advantageously carried out at temperatures of from 30 to 160° C., particularly preferably from 65 to 125° C., with temperatures in the upper part of this range being preferred for copolymers of relatively high density and temperatures in the lower part of this range being preferred for copolymers of lower density.

It is also possible to use a multizone reactor in which two polymerization zones are linked to one another and the polymer is passed alternately a plurality of times through these two zones, with the two zones also being able to have different polymerization conditions. Such a reactor is described, for example, in WO 97/04015 and WO 00/02929.

The different or else identical polymerization processes can also, if desired, be connected in series and thus form a polymerization cascade. A parallel arrangement of reactors using two or more different or identical processes is also possible. However, the polymerization is preferably carried out in a single reactor.

All documents mentioned are expressly incorporated by reference into the present patent application. All proportions and ratios in the present patent application are by weight based on the total weight of the corresponding mixtures, unless gas mixtures are concerned or unless indicated otherwise. In the case of gas mixtures, all figures are by volume, unless indicated otherwise.

The chromium content of the catalyst was determined photometrically via the peroxide complex.

The density of the polymer samples was determined in accordance with DIN EN ISO 1183-1, variant A.

The determination of the intrinsic viscosity $\eta$, which indicates the limit value of the viscosity number on extrapolation of the polymer concentration to zero, was carried out using an automatic Ubbelohde viscometer (Lauda PVS 1) at a concentration of 0.001 g/ml in decalin as solvent at 135° C. in accordance with ISO 1628-1: 1998.

The molar masses were determined by high-temperature gel permeation chromatography by means of a method based on DIN 55672 using 1,2,4-trichlorobenzene as solvent and a flow of 1 m/min at 140° C. Calibration was carried out by means of PE standards on an Waters 150 C. Evaluation of the data was carried out using the software Win-GPC from HS- Entwicklungsgesellschaft für wissenschaftliche Hard- und Software mbH, Ober-Hilbersheim. The determination of the molar mass distributions and the means Mn, Mw and $M_w/M_n$ derived therefrom was carried out by means of high-temperature gel permeation chromatography using a method based on DIN 55672 on a WATERS 150 C with the following columns connected in series: 3×SHODEX AT 806 MS, 1×SHODEX UT 807 and 1×SHODEX AT-G under the following conditions: solvent: 1,2,4-trichlorobenzene (stabilized with 0.025% by weight of 2,6-di-tert-butyl-4-methylphenol), flow: 1 mL/min, 500 μl injection volume, temperature: 135° C., calibration using PE standards. Evaluation was carried out by means of WIN-GPC. The columns were calibrated by means of polyethylene standards having molar masses of from 100 to $10^7$ g/mol. The weight average molar masses ($M_w$) and number average molar masses ($M_n$) of the polymers and also the ratios of weight average molar mass to number average molar mass ($M_w/M_n$) were determined.

The bulk density was measured on polymer powder in accordance with DIN 53468.

The melt mass flow rates $MFR_2$ (MI), $MFR_{21}$ (HLMI) were determined at a temperature of 190° C. and a weight of 2.16 or 21.6 kg in accordance with ISO 1133.

The fine dust content is the proportion of polymer particles which have a particle size of less than 125 μm. The particle size was determined by sieve analysis.

The invention is illustrated below by means of examples, without being restricted thereto.

EXAMPLE 1 AND COMPARATIVE EXAMPLE 1 a) Preparation of the Catalyst

The catalyst having a content of 1% by weight of chromium was prepared as described in EP A 0 589 350.

b) Activation:

The activation of the catalyst precursor was carried out at the calcination temperatures indicated in Table 1. 2.5% by weight of ammonium hexafluorosilicate (ASF), based on the total mass of the catalyst, were added. To carry out the activation, the catalyst precursor was heated to 350° C. over a period of one hour, maintained at this temperature for 1 hour, subsequently heated to the calcination temperature, maintained at this temperature for 2 hours and subsequently cooled, with cooling below a temperature of 350° C. being carried out under nitrogen.

c) Polymerization

The polymerizations were carried as suspension processes in isobutane in a 0.2 m³ PF loop reactor. The melt mass flow rate ($MFR_{21}$) and the density were set via the ethylene concentration or hexene concentration. The reactor pressure was 3.9 MPa.

In comparative example C1, pure Costelan AS 100 (0.44% by weight in hexane) was used in the polymerization, and in Example 1 an antistatic which had been prepared by mixing 2 parts of a 0.44% strength by weight solution of Costelan AS 100 (from Costenoble, Eschborn, Germany) in hexane with 1 part of a 0.40% strength by weight solution of trihexylaluminum (THA) in hexane was used. The polymerization conditions and results are summarized in Table 1.

TABLE 1

| Example | 1 | C1 |
| --- | --- | --- |
| Temperature [° C.] | 104 | 104 |
| Ethene [% by volume] | 16 | 15.9 |
| Hexene [% by volume] | 0.44 | 0.49 |
| Output [kg/h] | 30 | 30 |
| Productivity [g/kg] | 6900 | 3900 |
| $MFR_{21}$ [g/10 min] (powder) | 2.3 | 2.7 |
| $MFR_{21}$ [g/10 min] (granules) | 1.9 | 2.0 |
| Density [kg/m³] | 949 | 949 |
| Bulk density [kg/m³] | 500 | 480 |
| $M_w$/1000 [g/mol] | 503 | 513 |
| $M_w/M_n$ | 15.5 | 18 |
| Intr. viscosity [dl/g] | 4.5 | 4.4 |
| Cr content [% by weight] | 1 | 1 |
| ASF content [% by weight] | 2.5 | 2.5 |
| Activation temp. [° C.] | 520 | 520 |
| Fine dust content [% by weight] | 0.6 | 1.5 |
| Costelan AS 100* [ppm] | 0 | 9 |
| Costelan AS 100/THA* [ppm] | 9 | 0 |

*based on Costelan AS 100 in the polyethylene, weight ratio of Costelan AS 100:THA = 2:1

It can be seen from Table 1 that the antistatic mixture of the invention leads to a higher productivity and bulk density combined with a lower fine dust content and MFR drop (difference between the MFR measured on the granules after homogenization and that measured on the powder) of the kneading material. The poisoning effect of the antistatic mixture with THA on the catalyst is significantly lower than that of pure antistatic, and the antistatic action is surprisingly even improved.

The mixture of the invention enables the production costs to be considerably lowered as a result of the higher catalyst efficiency and the higher bulk density (i.e. higher reactor polymer density) and at the same time enables improved product quality to be achieved. Processes of the ungranulated polymer powder can increase the throughput of processing plants as a result of the higher bulk density.

EXAMPLE 2

Mixtures of Costelan AS 100 with trihexylaluminum (THA) were prepared. Both Costelan AS 100 and also THA were present as dilute solutions in hexane, and the solutions were mixed in a ratio of 2:1. A homogeneous solution was obtained in all cases. All measurements were carried out at a temperature of 20° C. The concentrations of Costelan AS 100 and THA in hexane in the mixture are shown in Table 2.

Immediately after mixing, the conductivity of the solutions was measured. The results are shown in Table 2.

TABLE 2

Conductivity of the THA/Costelan solutions

| Antistatic | Costelan AS 100% by weight in hexane | THA % by weight in hexane | Conductivity |
| --- | --- | --- | --- |
| THA | 0 | 0.4 | 0.003 μS/cm |
| Costelan AS 100 | 0.44 | 0 | 0.026 μS/cm |
| Costelan AS 100/THA | 0.44 | 0.4 | 0.043 μS/cm |
| Costelan AS 100 | 0.77 | 0 | 0.043 μS/cm |
| Costelan AS 100/THA | 0.77 | 0.4 | 0.055 μS/cm |

It can be seen from Table 2 that the novel formulation has a significantly improved conductivity at low concentrations. It is surprisingly found that the mixtures of THA and Costelan AS 100 have a conductivity which is higher than the sum of the individual components.

The invention claimed is

1. A process for preparing an antistatic for olefin polymerization by contacting, prior to polymerization,
   a) a mixture of antistatically acting compounds comprising at least one hydrogen atom bound to a non metallic heteroatom with at least one of the antistatically acting compounds having a molar mass of at least 100 g/mol with
   b) at least one metal alkyl in an amount which is sufficient to react completely with the at least one hydrogen atom bound to a heteroatom, wherein the mixture of antistatically acting compounds and the at least one metal alkyl are each present in a concentration of at least 0.01% by weight during contacting and the contact time of the metal alkyl with the antistatically acting compounds is from 10 s to 10 h up to entry into a polymerization reactor.

2. The process according to claim 1, wherein the mixture of antistatically acting compounds comprises a functional group selected from among —OH, —COOH, —$NH_2$, —$NHR^1$, —SH, —$PH_2$, —$PHR^1$ and —$SO_3H$, where $R^1$ is an alkyl, aryl, alkylaryl or arylalkyl radical in which one or more carbon atoms may also he replaced by heteroatoms.

3. The process according to claim 1, wherein the mixture of antistatically acting compounds comprises a polysulfone copolymer, a polymeric polyamine and an nil-soluble sulfonic acid.

4. The process according to claim 1, wherein the metal alkyl is selected from among aluminum alkyls, lithium alkyls, boron alkyls and zinc alkyls.

5. An antistatic for olefin polyrnerization which is produced by the process according to claim 1.

6. The antistatic according to claim 5 comprising the metal alkylsulfonate of an oil-soluble sulfonic acid.

7. The antistatic according to claim 6 comprising a polysulfone copolymer and a polymeric polyamine.

8. A process for the polymerization of 1-olefins at temperatures of from 20 to 200° C. and pressures of from 0.1 to 20 MPa in a polymerization reactor in the presence of a polymerization catalyst and the antistatic according to claim 5.

9. The process according to claim 8, wherein the antistatic is prepared by contacting of the metal alkyl with the antistatically acting compounds immediately before or during introduction into the reactor.

10. The process according to claim 8, wherein the polymerization catalyst comprises at least one Ziegler-Natta catalyst, a Phillips catalyst or a catalyst comprising a transition metal coordination compound, a metallocene and/or a late transition metal complex.

11. The process according to claim 8, wherein ethylene is homopolymerized or ethylene is copolymerized with up to 40% by weight, based on the total polymer, of propylene, 1-butene, 1-hexene or 1-octene.

12. The process according to claim 8, wherein propylene is homopolymerized or propylene is copolymerized with up to 40% by weight, based on the total polymer, of ethylene, 1-butene, 1-hexene or 1-octene.

13. The process of claim 8, wherein the polymerization carried out continuously.

14. The process of claim 13, wherein the antistatic is prepared by contacting of the metal alkyl with the antistatically acting compounds immediately before or during introduction into the reactor.

15. The process of claim 14, wherein the contact time of the metal alkyl with the antistatically acting compounds is from 10 s to 10 h up to entry into the polymerization reactor.

16. The process of claim 13, wherein the polymerization catalyst comprises at least one Ziegler-Natta catalyst, a Phillips catalyst or a catalyst comprising a transition metal coordination compound, a metallocene an or a late transition metal complex.

17. The process of claim 13, wherein ethylene is homopolymerized or ethylene is copolymerized with up to 40% by weight, based on the total polymer, of propylene, 1-butene, 1-hexene or 1-octene.

18. The process of claim 13, wherein propylene is homopolymerized or propylene is copolymerized with up to 40% by weight, based on the total polymer, of ethylene, 1-butene, 1-hexene or 1-octene.

19. The process of claim 13, wherein the polymerization reactor comprises a gas-phase fluidized bed.

* * * * *